United States Patent
Buchwald et al.

(10) Patent No.: US 9,595,682 B2
(45) Date of Patent: Mar. 14, 2017

(54) ORGANIC CONDUCTIVE MATERIALS AND DEVICES

(71) Applicant: Massachusetts Institute of Technology, Cambridge, MA (US)

(72) Inventors: Stephen L. Buchwald, Newton, MA (US); Timothy M. Swager, Newton, MA (US); Georgiy Teverovskiy, St. Louis Park, MN (US); Mingjuan Su, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 486 days.

(21) Appl. No.: 14/067,342

(22) Filed: Oct. 30, 2013

(65) Prior Publication Data

US 2014/0124762 A1    May 8, 2014

Related U.S. Application Data

(60) Provisional application No. 61/720,120, filed on Oct. 30, 2012.

(51) Int. Cl.
*H01L 51/00* (2006.01)
*C07D 487/18* (2006.01)
*H01L 51/50* (2006.01)

(52) U.S. Cl.
CPC ........ *H01L 51/0072* (2013.01); *C07D 487/18* (2013.01); *H01L 51/0073* (2013.01); *H01L 51/0074* (2013.01); *H01L 51/5012* (2013.01); *H01L 51/5048* (2013.01); *Y02E 10/549* (2013.01)

(58) Field of Classification Search
None
See application file for complete search history.

(56) References Cited

U.S. PATENT DOCUMENTS

| | | |
|---|---|---|
| 4,885,211 A | 12/1989 | Tang et al. |
| 5,059,861 A | 10/1991 | Littman et al. |
| 5,059,862 A | 10/1991 | Littman et al. |
| 5,247,190 A | 9/1993 | Friend et al. |
| 5,608,287 A | 3/1997 | Hung et al. |
| 5,677,572 A | 10/1997 | Hung et al. |
| 5,703,436 A | 12/1997 | Forrest et al. |
| 5,714,838 A | 2/1998 | Haight et al. |

(Continued)

FOREIGN PATENT DOCUMENTS

| | | | |
|---|---|---|---|
| EP | 1076368 A2 | 2/2001 | |
| KR | 10-2012-0021448 | * 3/2012 | ............. C09K 11/06 |

(Continued)

OTHER PUBLICATIONS

Machine English translation of KR 10-2012-0021448, Dec. 10, 2015.*
Van Dijken et al., Carbazole compounds as host materials for triplet emitters in organic light-emitting diodes: polymer hosts for high-efficiency light-emitting diodes. J Am Chem Soc. Jun. 23, 2004;126(24):7718-27.

(Continued)

*Primary Examiner* — J. L. Yang
(74) *Attorney, Agent, or Firm* — Wolf, Greenfield & Sacks, P.C.

(57) ABSTRACT

Embodiments described herein relate to compositions including iptycene-based structures and extended iptycene structures. In some embodiments, the compositions may be useful in organic light-emitting diodes (OLEDs), organic photovoltaics, and other devices.

20 Claims, 5 Drawing Sheets

(56) References Cited

U.S. PATENT DOCUMENTS

| | | | |
|---|---|---|---|
| 5,739,545 | A | 4/1998 | Guha et al. |
| 5,776,622 | A | 7/1998 | Hung et al. |
| 5,776,623 | A | 7/1998 | Hung et al. |
| 5,837,391 | A | 11/1998 | Utsugi |
| 5,969,474 | A | 10/1999 | Arai |
| 5,981,306 | A | 11/1999 | Burrows et al. |
| 6,137,223 | A | 10/2000 | Hung et al. |
| 6,140,763 | A | 10/2000 | Hung et al. |
| 6,172,459 | B1 | 1/2001 | Hung et al. |
| 6,278,236 | B1 | 8/2001 | Madathil et al. |
| 6,284,393 | B1 | 9/2001 | Hosokawa et al. |
| 7,183,010 | B2 | 2/2007 | Jarikov |
| 2004/0265622 | A1* | 12/2004 | Sadasivan ............... B82Y 20/00 428/690 |
| 2009/0105488 | A1 | 4/2009 | Cheng et al. |
| 2009/0167166 | A1 | 7/2009 | Bach et al. |
| 2011/0237804 | A1 | 9/2011 | Tanaka et al. |

FOREIGN PATENT DOCUMENTS

| | | |
|---|---|---|
| WO | WO 00/70655 A2 | 11/2000 |
| WO | WO 01/41512 A1 | 6/2001 |
| WO | WO 01/93642 A1 | 12/2001 |

OTHER PUBLICATIONS

Brunner et al., Carbazole compounds as host materials for triplet emitters in organic light-emitting diodes: tuning the HOMO level without influencing the triplet energy in small molecules. J Am Chem Soc. May 19, 2004;126(19):6035-42.

Schmidt et al., Occurrence, biogenesis, and synthesis of biologically active carbazole alkaloids. Chem Rev. Jun. 13, 2012;112(6):3193-328. Epub Apr. 5, 2012.

Uoyama et al., Highly efficient organic light-emitting diodes from delayed fluorescence. Nature. Dec. 13, 2012;492(7428):234-8.

Chou et al., Triptycene derivatives as high-Tg host materials for various electrophosphorescent devices. J Mater Chem. Jan. 12, 2010;20(4):798-805.

International Search Report and Written Opinion for International Application No. PCT/US2013/067503 mailed Feb. 21, 2014.

Hart, Iptycenes, cuppendophanes and cappedophanes. Pure Applied Chemistry. 1993; 65(1):27-34.

Shahlai et al., Synthesis of supertriptycene and two related iptycenes. Journal of Organic Chemistry. 1991; 56:6905-6912.

Teverovskiy et al., Palladium-catalyzed bond forming reactions involving weak nucleophiles and applications thereof. Disclosure at Dow Chemical, Midland, MI; Nov. 1, 2012.

International Preliminary Report on Patentability mailed May 14, 2015 for PCT/US2013/067503.

* cited by examiner

R = H, O-butyl, CF₃           R = H, O-butyl, CF₃

R' is phenyl substituted with fluoro, cyano, methyl, OCF₃, SCF₃, SF₅, or R' is one of the following compounds:

ORGANIC CONDUCTIVE MATERIALS AND DEVICES

RELATED APPLICATIONS

This application claims priority under 35 U.S.C. §119(e) to co-pending U.S. Provisional Application Ser. No. 61/720,120, filed Oct. 30, 2012, the contents of which are incorporated herein by reference in its entirety for all purposes.

FIELD OF THE INVENTION

Embodiments described herein relate to compositions and devices including iptycene-based materials.

BACKGROUND OF THE INVENTION

For organic light-emitting diodes, efficient energy or charge transfer from a host species to an emissive guest species is desirable. To achieve this, host materials having a high triplet energy relative to the guest species and high thermal stability have been pursued, but to date remain a challenge to develop. Various classes of materials have been studied for use as host materials, including carbazole-derived materials. While many carbazoles have sufficiently high triplet states, they are often undesirably crystalline, insoluble, and difficult to process.

SUMMARY OF THE INVENTION

Compositions and devices are provided comprising iptycene-based compounds are provided. In some cases, the composition comprises an iptycene core and at least one optionally substituted heterocyclyl or optionally substituted heteroaryl moiety rigidly bonded to the iptycene core, wherein the optionally substituted heterocyclyl or optionally substituted heteroaryl moiety defines at least a portion of the iptycene core.

In some cases, the device comprises an iptycene-based compound comprising an iptycene core and at least one heterocyclyl or heteroaryl moiety bonded to the iptycene core, wherein the heterocyclyl or heteroaryl moiety is substituted with at least one electron-withdrawing group and the iptycene-based compound exhibits a solid state singlet-triplet energy gap of about 1 kcal/mol or less.

Figure 1:
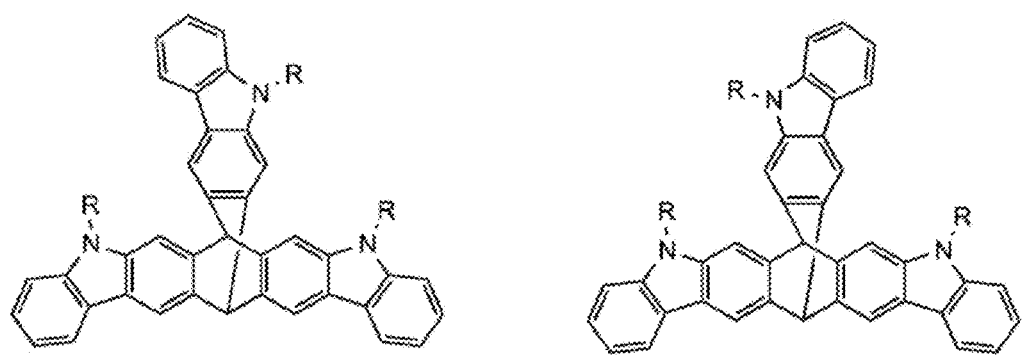
FIG. 1 shows examples of iptycene-based compounds.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

Embodiments described herein relate to compositions including iptycene-based structures and extended iptycene structures. In some cases, the iptycene-based structure includes various moieties having desirable physical and electronic properties. In some embodiments, the compositions may be useful in organic light-emitting diodes (OLEDs), organic photovoltaics, and other devices. An advantageous feature of embodiments described herein is the ability to tune the electronic properties of the compositions in order to suit a particular application. For example, compositions described herein may exhibit thermally activated delayed fluorescence (TADF) and may be useful as chromophores in OLED devices. In other cases, the compositions may exhibit high-lying triplet states and may be able to trap various triplet emitters, making them attractive host materials for OLED devices. In some cases, the composition may also be readily soluble and processable, and exhibit excellent thermal stability.

In some cases, the composition may include an iptycene-based structure having various functional groups arranged at specific locations within the iptycene-based structure to generate a desired electronic structure or to produce desired electronic properties. For example, arrangement of various electron-withdrawing or electron-deficient groups and/or electron-donating or electron-rich groups within the iptycene-based structure may advantageously create low overlap between the highest occupied molecular orbital (HOMO) and the lowest unoccupied molecular orbital (LUMO), relative to previous compositions. This may result in iptycene-based structures having a relatively small energy gap ($\Delta E_{ST}$) between the lowest singlet and triplet excited states, allowing for TADF with high photoluminescence efficiency (e.g., high quantum yield) and extended lifetimes.

In some cases, the iptycene-based structure may include a first portion containing one or more electron-withdrawing groups and a second portion lacking such electron-withdrawing groups. In some cases, the second portion may include electron-donating or electron-rich groups. Some embodiments may involve an iptycene-based structure having an electron donor portion optionally containing one or more electron-donating groups, and an electron acceptor portion covalently bonded to the electron donor portion and containing one or more electron-withdrawing groups.

Some embodiments provide compositions including an iptycene-based compound comprising an iptycene core and one or more optionally substituted heterocyclyl or optionally substituted heteroaryl moieties rigidly bonded to the iptycene-based core. In some cases, a group may be rigidly bonded to a core such that the group does not easily rotate about a bond axis, e.g., a bond that binds the group to the core. In one embodiment, the group rotates no more than about 180°, no more than about 120°, no more than about 60°, no more than about 30°, or less, about a bond that binds the group to the core. In some cases, a group may be rigidly bound to the core via two covalent bonds. For example, a group may be fused to the core via covalent bonds to two adjacent atoms of the core. In some embodiments, the heterocyclyl or heteroaryl groups may be substituted with one or more electron-withdrawing groups.

In some cases, the heterocyclyl or heteroaryl moiety may be rigidly bonded to the iptycene core and/or may define at least a portion of the iptycene core. For example, the iptycene core may include one or more phenyl rings that may be extended or functionalized so as to form a heterocyclyl or heteroaryl moiety (e.g., a carbazole group) which includes one or more phenyl rings of the iptycene core. FIG. 1 shows examples of a compound as described herein, where the compound includes three carbazole moieties rigidly bonded to a triptycene core such that the phenyl rings of the carbazole groups define, or overlap with, phenyl groups of the triptycene core.

Figure 3:
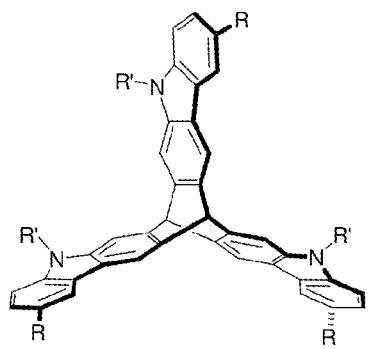
FIG. 3 shows examples of iptycene-based compound including substituted carbazole moieties.
Figure 3:
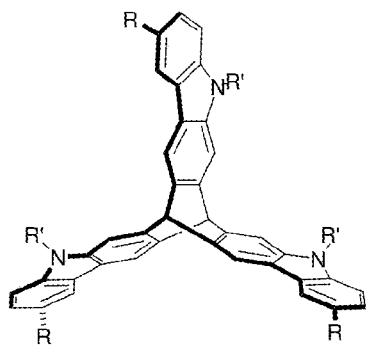
Figure 3:
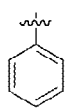
Figure 3:
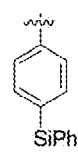
Figure 3:
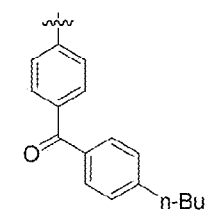
Figure 3:
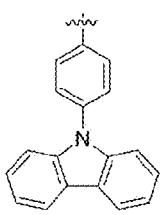
Figure 3:
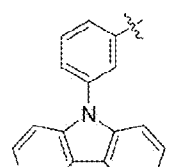
Figure 3:
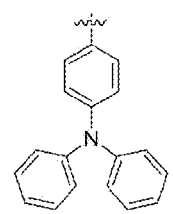
Figure 3:
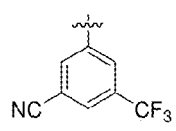
Figure 3:
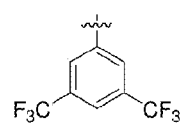
Figure 3:
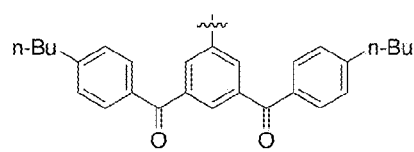
Figure 3:
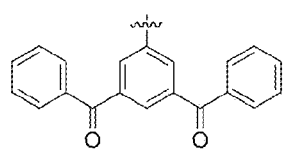
Figure 3:
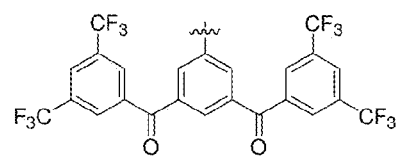
Figure 3:
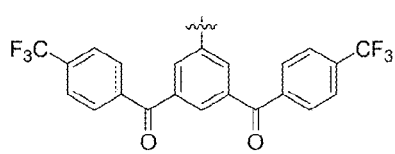
Figure 3:
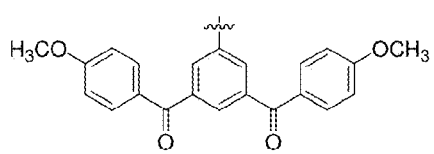

Some embodiments may involve an iptycene-based structure containing one or more carbazole moieties substituted with electron-withdrawing groups. In some embodiments, the iptycene-based structure includes a carbazole moiety substituted with a phenyl group at the carbazole nitrogen atom, the phenyl group being meta-substituted (relative to the carbazole nitrogen atom) with an electron-withdrawing group. In some cases, the iptycene-based structure includes a carbazole moiety substituted with a phenyl group at the carbazole nitrogen atom, the phenyl group being di-meta-substituted (relative to the carbazole nitrogen atom) with electron-withdrawing groups. That is, both meta positions of the phenyl ring on the carbazole nitrogen atom may be substituted with an electron-withdrawing group. In some embodiments, the carbazole moiety may be attached to the iptycene-based structure. In some embodiments, the carbazole moiety may rigidly bonded to an iptycene core and may define at least a portion of the iptycene core. FIG. 3 includes examples of iptycene-based structures containing carbazole moieties rigidly bonded to the iptycene core and electron-withdrawing groups positioned meta to the carbazole nitrogen atom.

In some embodiments, the iptycene-based compound includes a triptycene core. In some embodiments, the iptycene-based compound includes a pentiptycene core. It should be understood that the compound may include other, extended iptycene cores which have, for example, additional numbers of branches, arene planes, and/or extended bridgehead structures. For example, the central phenyl ring of a pentiptycene core may have an extended structure such as a central anthracene ring system. The synthesis of iptycenes and like molecules is described in, for example, Hart, "Iptycenes, Cuppendophanes and Cappedophanes," Pure and Applied Chemistry, 65(1):27-34 (1993); and Shahlia et al., "Synthesis of Supertriptycene and Two Related Iptycenes," Journal of Organic Chemistry, 56:6905-6912 (1991), the contents of which are incorporated herein by reference. In some embodiments, the iptycene core may be synthesized via a Diels-Alder reaction between an anthracene species and a benzyne species.

In some cases, iptycene-based compounds and structures disclosed herein may exhibit a solid state singlet-triplet energy gap of 5 kcal/mol or less, 4.5 kcal/mol or less, 4 kcal/mol or less, 3.5 kcal/mol or less, 3 kcal/mol or less, 2.5 kcal/mol or less, 2 kcal/mol or less, 1.5 kcal/mol or less, 1 kcal/mol or less, or 0.5 kcal/mol or less. For example, the iptycene-based compound may exhibit a singlet-triplet energy gap in the range of about 0.1 to about 1 kcal/mol, about 0.1 to about 0.5 kcal/mole, or about 0.4 to about 0.5 kcal/mol, in solid state. In some cases, the iptycene-based compound may exhibit a solid state singlet-triplet energy gap of about 0.1 kcal/mol. In some cases, the iptycene-based compound may exhibit a solid state singlet-triplet energy gap of about 0.2 kcal/mol. In some cases, the iptycene-based compound may exhibit a solid state singlet-triplet energy gap of about 0.3 kcal/mol. In some cases, the iptycene-based compound may exhibit a solid state singlet-triplet energy gap of about 0.4 kcal/mol. In some cases, the iptycene-based compound may exhibit a solid state singlet-triplet energy gap of about 0.5 kcal/mol. In some cases, the iptycene-based compound may exhibit a solid state singlet-triplet energy gap of about 0.6 kcal/mol. In some cases, the iptycene-based compound may exhibit a solid state singlet-triplet energy gap of about 0.7 kcal/mol. In some cases, the iptycene-based compound may exhibit a solid state singlet-triplet energy gap of about 0.8 kcal/mol. In some cases, the iptycene-based compound may exhibit a solid state singlet-triplet energy gap of about 0.9 kcal/mol. In some cases, the iptycene-based compound may exhibit a solid state singlet-triplet energy gap of about 1 kcal/mol. The solid state singlet-triplet energy gap of a material may be determined by calculating the energy difference between singlet ($S_1$) and triplet ($T_1$) energy levels ($\Delta E_{ST}$) of the material in solid state, as calculated from the onsets of the fluorescence and phosphorescence spectra of the material.

In some cases, the iptycene-based compounds and structures disclosed herein exhibit an external quantum yield of greater than 25%, such as about 30%, about 35%, about 40%, about 45%, about 50%, about 55%, about 60%, or greater. In some cases, devices incorporating the iptycene-based compounds and structures disclosed herein may exhibit an internal quantum yield of about 70%, about 75%, about 80%, about 85%, about 90%, or greater.

Devices incorporating the iptycene-based compounds disclosed herein are also provided. For example, the iptycene-based compound may be useful as a chromophore in a luminescence-based device such as an OLED. In some cases, the iptycene-based compound may include an iptycene core and at least one heterocyclyl or heteroaryl moiety bonded to the iptycene core. The heterocyclyl or heteroaryl moiety may be substituted with at least one electron-withdrawing group such that the iptycene-based compound exhibits a singlet-triplet energy gap of 5 kcal/mol or less (e.g., 1 kcal/mol or less) when the iptycene-based compound in solid state. Such devices may advantageously exhibit TADF with increased quantum yields.

In some embodiments, the iptycene-based compound has one of the following structures,

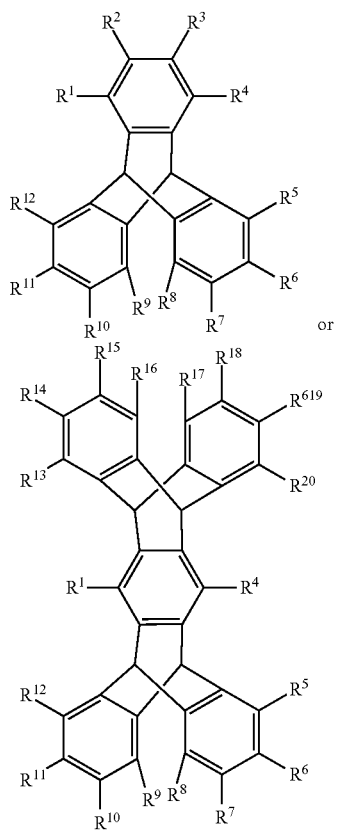

wherein:

$R^1$-$R^{20}$ can be the same or different and are hydrogen, halo, hydroxyl, amino, alkyl, heteroalkyl, alkenyl, alkynyl, aryl, heteroaryl, heterocyclyl, or a carbonyl group, any of which is optionally substituted, or, any two adjacent groups of $R^1$-$R^{20}$ can be joined together to form an optionally substituted ring, provided that two adjacent groups of $R^1$-$R^{20}$ are joined together to form at least one optionally substituted heterocyclic group or at least one optionally substituted heteroaryl group. In some cases, $R^2$ and $R^3$, $R^6$ and $R^7$, $R^{10}$ and $R^{11}$, $R^{14}$ and $R^{15}$, and/or $R^{18}$ and $R^{19}$ are joined together to form an optionally substituted heterocyclic group or an optionally substituted heteroaryl group. For example, two adjacent groups of $R^1$-$R^{20}$ may be joined together to form a ring, such that a carbazole moiety is formed including the phenyl ring of the core iptycene structure.

In some cases, the compound has the following formula,

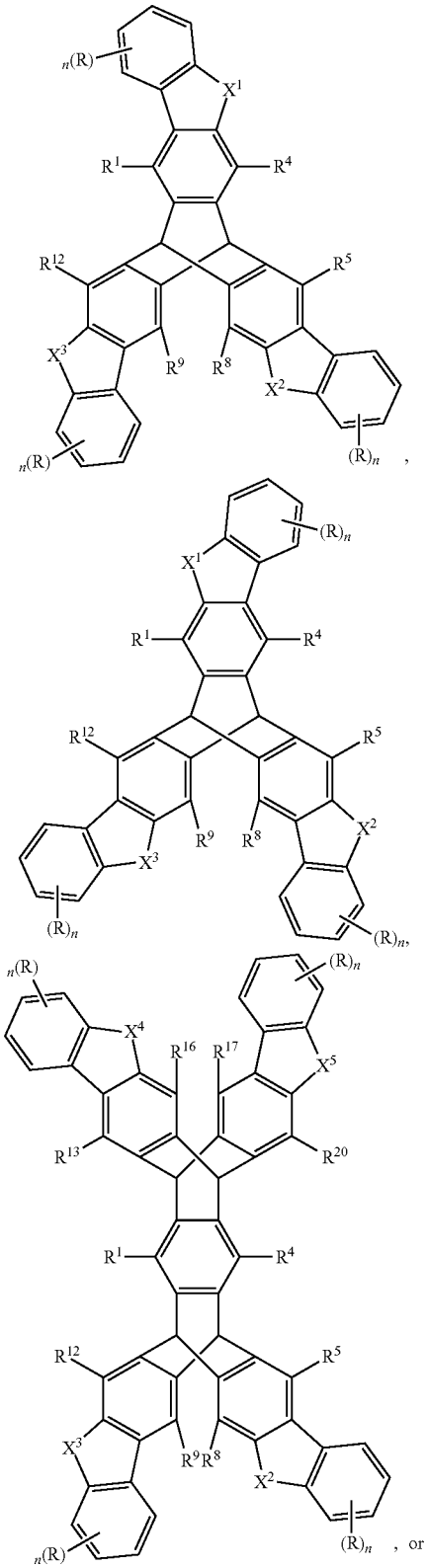

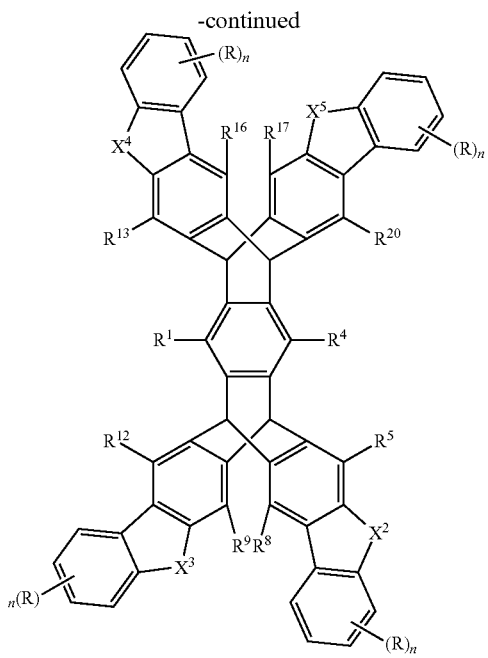

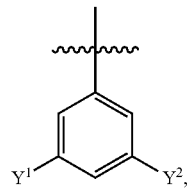

wherein $Y^1$ and $Y^2$ can be the same or different and are hydrogen, halo (e.g., fluoro), cyano, fluoroalkyl, fluoroalkoxy, or a carbonyl group. In some cases, R' is a group having the following formula,

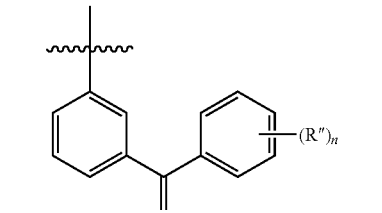

or

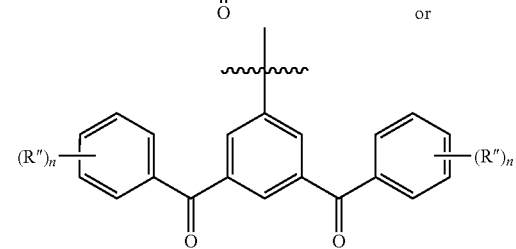

wherein R" is alkyl, fluoroalkyl, alkoxy, fluoroalkoxy, and n is 0-5.

In some embodiments, R' is a group having the following formula,

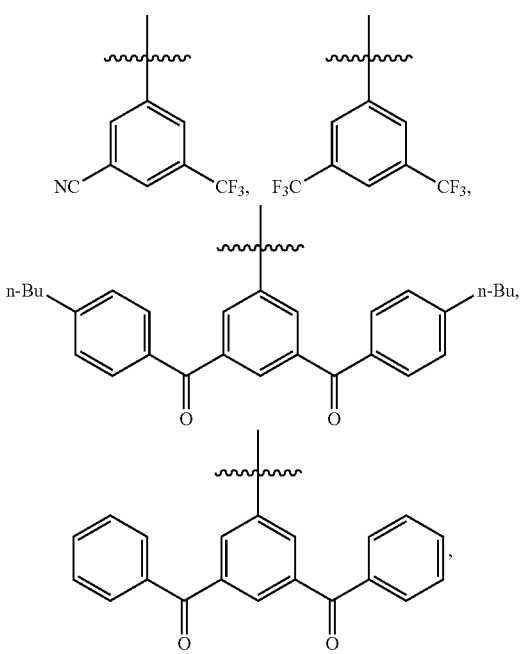

wherein:

$X^1$-$X^5$ can be the same or different and are heteroatoms or metal atoms, any of which is optionally substituted or optionally bonded to a polymer;

$R^1$, $R^4$, $R^5$, $R^8$, $R^9$, $R^{12}$, $R^{13}$, $R^{16}$, $R^{17}$, and $R^{20}$ can be the same or different and are hydrogen, halo, hydroxyl, amino, alkyl, heteroalkyl, alkenyl, alkynyl, aryl, heteroaryl, heterocyclyl, or a carbonyl group, any of which is optionally substituted or optionally bonded to a polymer;

each R can be the same or different and is a substituent, optionally substituted or optionally bonded to a polymer; and n is an integer from 0-4.

In some embodiments, $R^1$, $R^4$, $R^5$, $R^8$, $R^9$, $R^{12}$, $R^{13}$, $R^{16}$, $R^{17}$, and $R^{20}$ are hydrogen.

In some embodiments, $X^1$-$X^5$ can be the same or different and are Si, O, S, or N(R'), or Si, wherein R' is H, alkyl, heteroalkyl, alkenyl, heteroalkenyl, alkynyl, aryl, heteroaryl, heterocyclyl, or a carbonyl group, any of which is optionally substituted.

In some embodiments, each $X^1$-$X^5$ is NH. In some embodiments, each $X^1$-$X^5$ is N(R'), wherein R' is an optionally substituted aryl or an optionally substituted heteroaryl. For example, R' may be phenyl substituted with one or more electron-withdrawing groups, such as halo (fluoro), cyano, nitro, fluoroalkyl, fluoroalkoxy, fluoroaryl, or a carbonyl group. In some embodiments, R' is phenyl substituted with fluoro, cyano, $CF_3$, $OCF_3$, $SCF_3$, $SF_5$, or a carbonyl group.

In some embodiments, the phenyl ring is substituted with electron-withdrawing groups at one or both meta positions, relative to the nitrogen atom of the group N(R').

For example, R' in any of the structures disclosed herein may be a group having the following formula, -continued

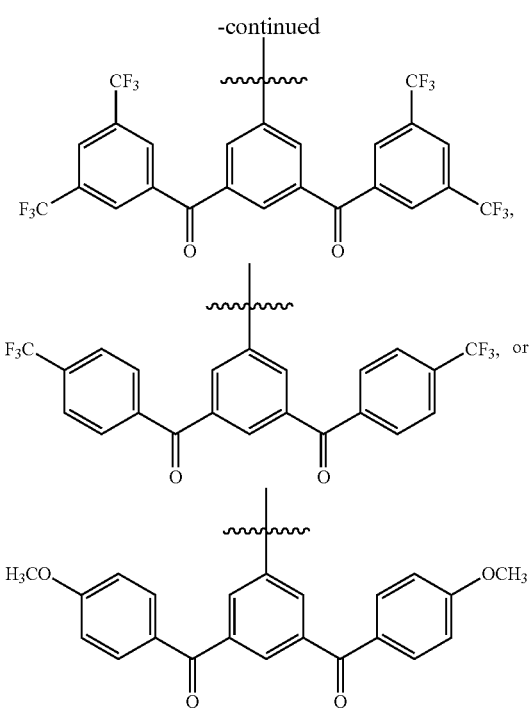

It should also be understood that in certain embodiments it may be desirable for R' to be phenyl substituted with one or more electron-donating groups, such as alkyl, alkoxy, aryl, heteroaryl, P(aryl)$_3$, or Si(aryl)$_3$. For example, R' can be phenyl substituted with methyl, phenyl,

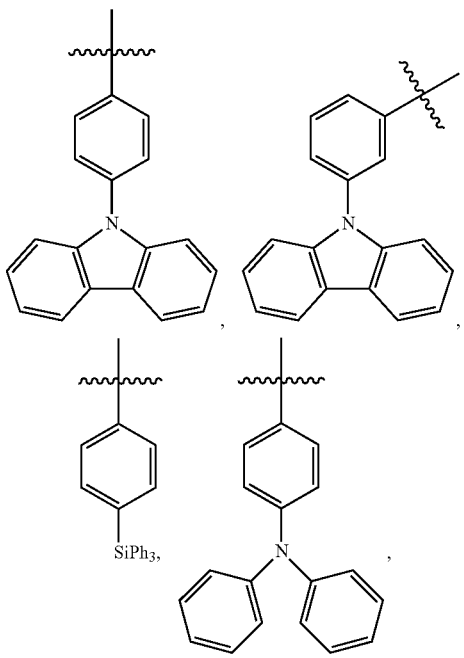

or combinations thereof.

In the embodiments described herein, each R can be the same or different and can be alkyl, alkoxy, alkyl sulfanyl, alkylamino, dialkylamino, alkenyl, alkynyl, cycloalkyl, an cycloalkenyl, an heterocyclyl, an aryl, an heteroaryl, an aralkyl, an heteroaralkyl, a haloalkyl, —C(O)NR$^a$R$^b$, —NR$^c$C(O)R$^d$, halo, —OR$^c$, cyano, nitro, haloalkoxy, —C(O)R$^c$, —NR$^a$R$^b$, —SR$^c$, —C(O)OR$^c$, —OC(O)R$^c$, —NR$^c$C(O)NR$^a$R$^b$, OC(O)NR$^a$R$^b$, NR$^c$C(O)OR$^d$, S(O)$_p$R$^c$, or —S(O)$_p$NR$^a$R$^b$, wherein R$^a$ and R$^b$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl; or R$^a$ and R$^b$ taken together with the nitrogen to which they are attached form optionally substituted heterocyclyl or optionally substituted heteroaryl; and R$^c$ and R$^d$ for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl.

In some cases, R can be the same or different and is halo. In some cases, each R is fluoro.

In some cases, R is a polymer, or a group that forms a bond to a polymer.

In one set of embodiments, the iptycene-based compound has the following structure,

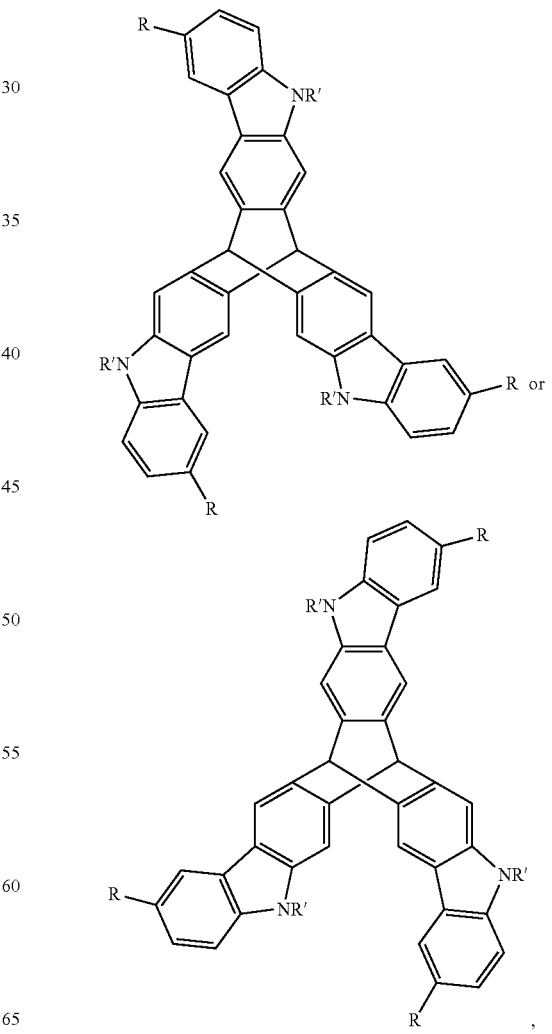

wherein:

R is hydrogen, alkyl, alkoxy, fluoroalkyl, or fluoroalkoxy; and

R' is a group having the following formula,

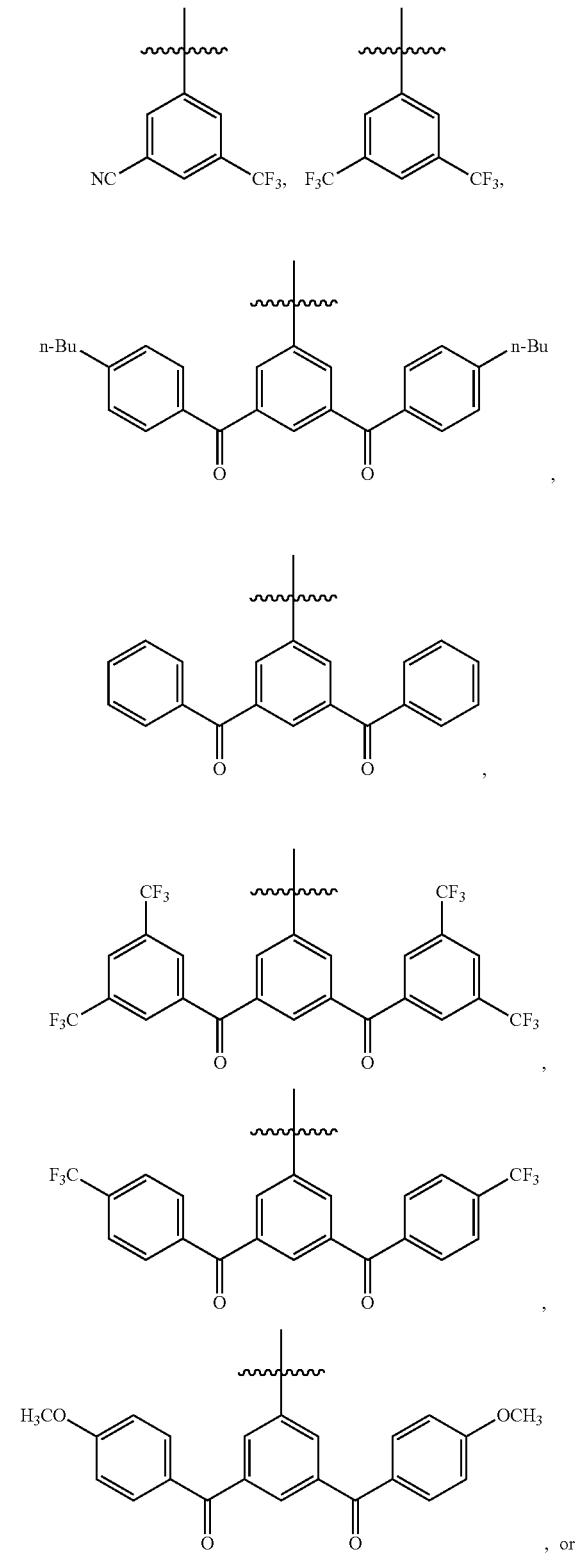

, or

-continued

[structure with (CH$_2$)$_n$H]

wherein n is 1 or greater. In some cases, n is 1-10.

In some cases, R is hydrogen. In some cases, R is O-butyl. In some cases, R is CF$_3$.

Figure 2A:
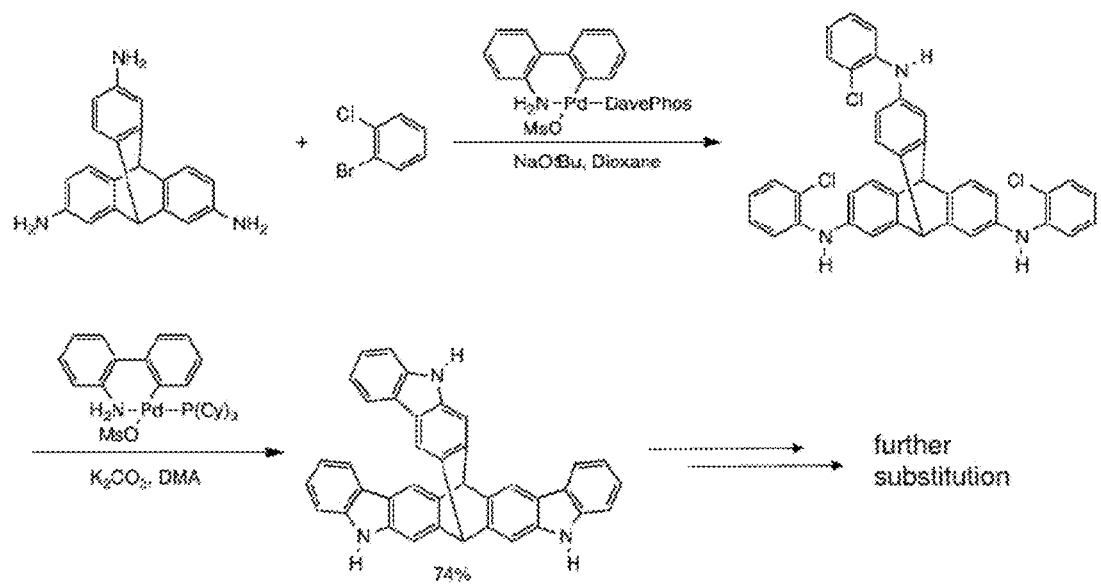
FIG. 2 shows (a) the synthesis of an iptycene-based compound including carbazole moieties, and (b) further substitution of the iptycene-based compound including carbazole moieties.
Figure 2B:
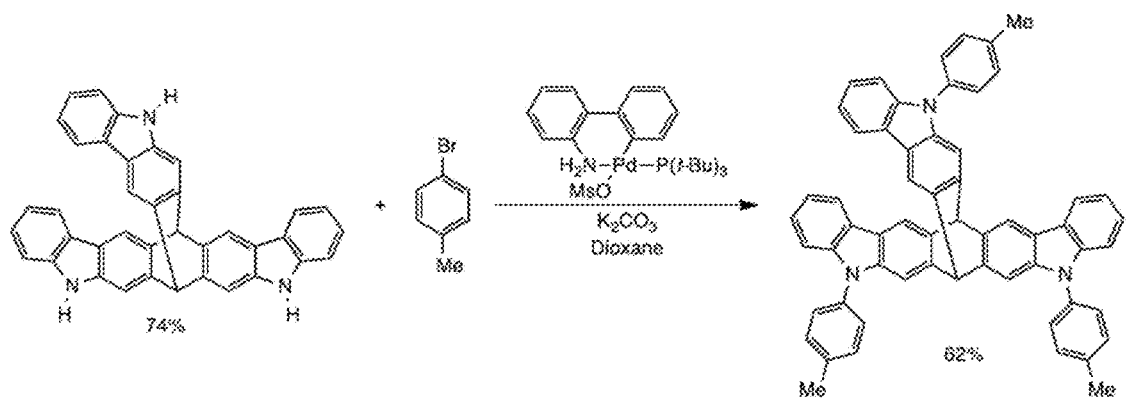

Methods for synthesizing such compounds are described herein, as well as in Chou et al., J. Mater. Chem. 2010, 20, 798-805; Schmidt et al., Chem. Rev. 2012, 112(6), 3193-3328; U.S. Publication No. 2009/0105488; and Li et al., *Organic Light-Emitting Materials and Devices*, Boca Raton: Taylor & Francis Group, 2007, the contents of which are incorporated herein by reference. FIG. 2A illustrates the synthesis of an iptycene-based compound including carbazole moieties, wherein an amino-substituted triptycene core is substituted with halo-substituted aryl group via a transition-metal catalyzed cross-coupling reaction. The resulting compound may then be cyclized to form the carbazole moieties. The compound may be further substituted, for example, at the nitrogen of the carbazole groups. FIG. 2B shows one embodiment where the carbazole moieties may be functionalized with substituted aryl groups. FIG. 3 shows additional examples of substituted carbazole moieties within an iptycene-based compound.

Figure 4:
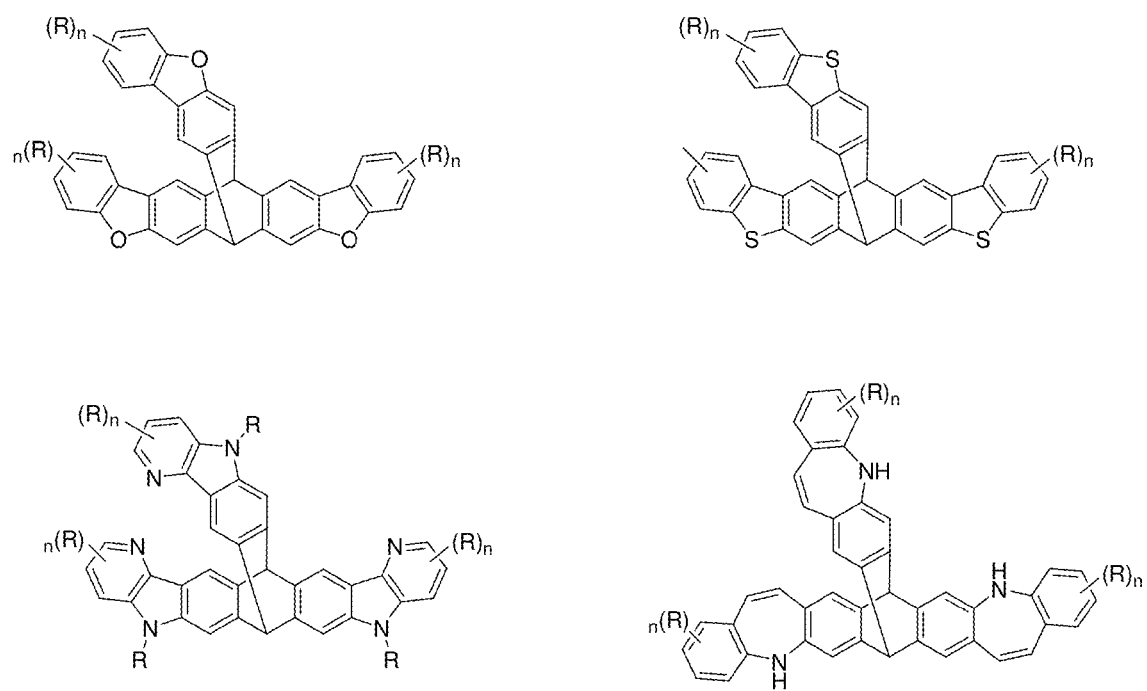
FIG. 4 shows examples of other iptycene-based compounds.

Compounds described herein may also include other optionally substituted heterocyclyl or heteroaryl groups rigidly bonded to the iptycene core. FIG. 4 shows embodiments where the compound including other nitrogen-containing, oxygen-containing, and sulfur-containing moieties appended to the iptycene core. In some cases, the compound may include a metal-containing group (e.g., Si-containing group) appended to the iptycene core.

In some cases, the iptycene-based compound may also be incorporated into a polymeric system. In some cases, the iptycene-based compound may be covalently bonded to a polymer. For example, iptycene-based compound may be covalently bonded to a polymer backbone via a pendant side group. In some cases, the iptycene-based compound may be positioned within a polymer backbone. For example, the iptycene-based compound may be bonded to a polymer via atoms of a heterocyclyl or heteroaryl group, and/or via bridgehead atoms of the iptycene core. In some embodiments, the iptycene-based compound may be dispersed within a polymer material (e.g., non-covalently dispersed), such as an acrylate or styrene polymer. In some cases, the iptycene-based compound may be combined with or dispersed within an electroactive polymer material (e.g., hole-transport polymer, electron-transport polymer).

Some embodiments may provide the iptycene-based compound combined with, dispersed within, covalently bonded to, coated with, formed on, or otherwise associated with, one or more materials (e.g., small molecules, polymers, metals, metal complexes, etc.) to form a film or layer in solid state. For example, the iptycene-based compound may be combined with an electroactive material to form a film. In some cases, the iptycene-based compound may be combined with a hole-transport polymer. In some cases, the iptycene-based compound may be combined with an electron-transport polymer. In some cases, the iptycene-based compound may be combined with a hole-transport polymer and an electron-transport polymer. In some cases, the iptycene-based compound may be combined with a copolymer comprising both hole-transport portions and electron-transport portions. In such embodiments, electrons and/or holes formed within the solid film or layer may interact with the iptycene-based compound.

Compositions described herein may be incorporated into various light-sensitive or light-activated devices, such as a OLEDs or photovoltaic devices. In some embodiments, the composition may be useful in facilitating charge transfer or energy transfer within a device and/or as a hole-transport material. The device may be, for example, an organic light-emitting diode (OLED), an organic integrated circuit (O-IC), an organic field-effect transistor (O-FET), an organic thin-film transistor (O-TFT), an organic light-emitting transistor (O-LET), an organic solar cell (O-SC), an organic optical detector, an organic photoreceptor, an organic field-quench device (O-FQD), a light-emitting electrochemical cell (LEC) or an organic laser diode (O-laser).

Figure 5:
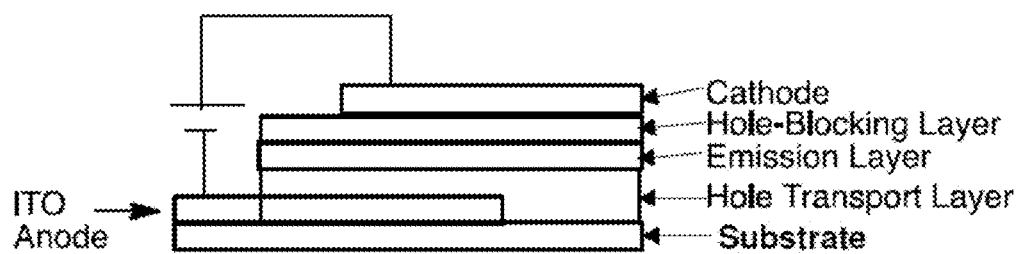
FIG. 5 shows a schematic representation of an organic light-emitting diode, according to one embodiment.

In some embodiments, the device may be an OLED including a composition as described herein. An OLED device typically includes a multilayer stack including a substrate, a cathode, an anode, and one or more layers including a material capable of emitting light, i.e., an emission layer or light-emitting layer. For example, the OLED device may include an emission layer containing a host material and a guest material, and within which excitons are produced. The layer may be positioned between and in electrical communication with an anode and a cathode. Other additional layers within an OLED may include electron-transporting layers, electron-injecting layer, hole-injecting layers, hole-transporting layers, exciton-blocking layers, spacer layers, connecting layers, hole-blocking layers, and the like. In some cases, the OLED may be a fluorescence-based OLED (e.g., TADF-based OLED). In some cases, the OLED may be a phosphorescence-based OLED. OLED devices, and methods for forming OLEDs, will be known to those of ordinary skill in the art. An illustrative embodiment of an OLED device is shown in FIG. 5.

In a typical OLED, holes and electrons injected into the device can recombine to form excitons, including, in the case of a phosphorescence-based OLED, both singlet and triplet excitons. In some cases, compositions described herein may facilitate the generation and/or retention of, a greater number of triplet excitons relative to singlet excitons. This may be desirable in certain OLEDS, as triplet excitons may not readily transfer their energy to singlet excited states and 100% internal quantum efficiency is theoretically possible. For example, OLEDs utilizing phosphorescent materials that emit from triplet excited states may exhibit relatively higher internal quantum efficiency.

In some cases, compositions described herein may serve as a chromophore within an OLED device.

In some embodiments, it may be desirable to include a hole-blocking layer within the OLED device to help confine the excitons and recombination events to the emission layer. Some examples of hole-blocking materials are described in International Publications WO 00/70655A2, WO 01/41512, and WO 01/93642. Those of ordinary skill in the art would be capable of selecting hole-transport materials, or mixtures thereof, suitable for use in embodiments described herein.

Those of ordinary skill in the art would be capable of selecting appropriate cathode materials for use in embodiments described herein. In some cases, the cathode material may be a conductive material. In some cases, the anode material may be substantially transparent. The anode material may be selected to promote electron injection at low voltage, and have effective stability. Examples of cathode materials are described in U.S. Pat. Nos. 4,885,211; 5,059,861; 5,059,862; 5,247,190; 5,703,436; 5,608,287; 5,837,391; 5,677,572; 5,776,622; 5,776,623; 5,714,838; 5,969,474; 5,739,545; 5,981,306; 6,137,223; 6,140,763; 6,172,459; 6,278,236; and 6,284,393; and European Patent No. 1076368. Cathode materials may be formed within the device using known methods, including thermal evaporation, electron beam evaporation, ion sputtering, or chemical vapor deposition. In some cases, the cathode may be patterned using known photolithographic processes.

In some embodiments, the anode may be selected to be substantially transparent opaque, or reflective. In one set of embodiments, the anode may be substantially transparent to the emission generated by the emission later. Examples of transparent anode materials include metal oxides such as indium-tin oxide (ITO), indium-zinc oxide (IZO), tin oxide, aluminum- or indium-doped zinc oxide, magnesium-indium oxide, and nickel-tungsten oxide, metal nitrides such as gallium nitride, metal selenides such as zinc selenide, and metal sulfides such as zinc sulfide. The anode may be formed within the devices using known techniques such as evaporation, sputtering, chemical vapor deposition, or electrochemical techniques. In some cases, the anode may be patterned using known photolithographic processes.

The substrate can be any material capable of supporting the device components as described herein. Preferably, the substrate material has a thermal coefficient of expansion similar to those of the other components of the device to promote adhesion and prevent separation of the layers at various temperatures. In some instances, materials with dissimilar thermal expansion coefficients may expand and contract at different rates and amounts with changes in temperature, which can cause stress and delamination of the layers. The substrate can either be light transmissive or opaque, depending on the intended direction of light emission. Examples of appropriate substrate materials may include glass, plastic, semiconductor materials such as silicon, ceramics, and circuit board materials.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The alkyl groups may be optionally substituted, as described more fully below. Examples of alkyl groups include, but are not limited to, methyl, ethyl, propyl, isopropyl, butyl, isobutyl, tert-butyl, 2-ethylhexyl, cyclopropyl, cyclobutyl, cyclopentyl, cyclohexyl, and the like. "Heteroalkyl" groups are alkyl groups wherein at least one atom is a heteroatom (e.g., oxygen, sulfur, nitrogen, phosphorus, etc.), with the remainder of the atoms being carbon atoms. Examples of heteroalkyl groups include, but are not limited to, alkoxy, poly(ethylene glycol)-, alkyl-substituted amino, tetrahydrofuranyl, piperidinyl, morpholinyl, etc. "Fluoroalkyl" groups are alkyl groups wherein at least one hydrogen is replaced with a fluoro group. In some cases, all hydrogen groups of an alkyl group are replaced with fluoro groups to form a fluoroalkyl group (e.g., $CF_3$).

The term "alkoxy" refers to —O-alkyl. A "fluoroalkoxy" group refers to —O-fluoroalkyl.

The terms "alkenyl" and "alkynyl" refer to unsaturated aliphatic groups analogous to the alkyl groups described above, but containing at least one double or triple bond respectively. The "heteroalkenyl" and "heteroalkynyl" refer to alkenyl and alkynyl groups as described herein in which one or more atoms is a heteroatom (e.g., oxygen, nitrogen, sulfur, and the like).

The term "aryl" refers to an aromatic carbocyclic group having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl), all optionally substituted. "Fluoroaryl" groups are aryl groups that are substituted with at least one fluoro group.

The terms "amine" and "amino" refer to both unsubstituted and substituted amines, e.g., a moiety that can be represented by the general formula: N(R')(R'')(R''') wherein R', R'', and R''' each independently represent a group permitted by the rules of valence.

The terms "acyl," "carboxyl group," or "carbonyl group" are recognized in the art and can include such moieties as can be represented by the general formula:

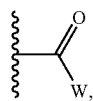

wherein W is H, OH, O-alkyl, O-alkenyl, or a salt thereof. Where W is O-alkyl, the formula represents an "ester." Where W is OH, the formula represents a "carboxylic acid." In general, where the oxygen atom of the above formula is replaced by sulfur, the formula represents a "thiolcarbonyl" group. Where W is a S-alkyl, the formula represents a "thiolester." Where W is SH, the formula represents a "thiolcarboxylic acid." On the other hand, where W is alkyl, aryl, or another carbon-containing substituent, the above formula represents a "ketone" group. Where W is hydrogen, the above formula represents an "aldehyde" group.

The terms "electron-withdrawing group," "electron-deficient group," and "electron-poor group" are recognized in the art and as used herein refer to a functionality which draws electrons to itself more than a hydrogen atom would at the same position. Examples of electron-withdrawing groups include carbonyl groups (e.g., ketone, esters, aldehydes), sulfonyl, fluoro, trifluoromethyl, nitro, cyano, and the like.

The terms "electron-donating group" and "electron-rich group" as used herein refer to a functionality which draws electrons to itself less than a hydrogen atom would at the same position. Exemplary electron-donating groups include amino, hydroxy, alkoxy, acylamino, acyloxy, alkyl, halides, and the like.

As used herein, the term "heterocycle" or "heterocyclyl" refers to a monocyclic or polycyclic heterocyclic ring that is either a saturated ring or an unsaturated non-aromatic ring. Typically, the heterocycle may include 3-membered to 14-membered rings. In some cases, 3-membered heterocycle can contain up to 3 heteroatoms, and a 4- to 14-membered heterocycle can contain from 1 to about 8 heteroatoms. Each heteroatom can be independently selected from nitrogen, which can be quaternized; oxygen; and sulfur, including sulfoxide and sulfone. The heterocycle may be attached via any heteroatom ring atom or carbon ring atom. Representative heterocycles include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. A heteroatom may be substituted with a protecting group known to those of ordinary skill in the art, for example, the hydrogen on a nitrogen may be substituted with a tert-butoxycarbonyl group. Furthermore, the heterocyclyl may be optionally substituted with one or more substituents (including without limitation a halogen atom, an alkyl radical, or aryl radical). Only stable isomers of such substituted heterocyclic groups are contemplated in this definition.

As used herein, the term "heteroaromatic" or "heteroaryl" means a monocyclic or polycyclic heteroaromatic ring (or radical thereof) comprising carbon atom ring members and one or more heteroatom ring members (such as, for example, oxygen, sulfur or nitrogen). Typically, the heteroaromatic ring has from 5 to about 14 ring members in which at least 1 ring member is a heteroatom selected from oxygen, sulfur, and nitrogen. In another embodiment, the heteroaromatic ring is a 5 or 6 membered ring and may contain from 1 to about 4 heteroatoms. In another embodiment, the heteroaromatic ring system has a 7 to 14 ring members and may contain from 1 to about 7 heteroatoms. Representative heteroaryls include pyridyl, furyl, thienyl, pyrrolyl, oxazolyl, imidazolyl, indolizinyl, thiazolyl, isoxazolyl, pyrazolyl, isothiazolyl, pyridazinyl, pyrimidinyl, pyrazinyl, triazinyl, triazolyl, pyridinyl, thiadiazolyl, pyrazinyl, quinolyl, isoquniolyl, indazolyl, benzoxazolyl, benzofuryl, benzothiazolyl, indolizinyl, imidazopyridinyl, isothiazolyl, tetrazolyl, benzimidazolyl, benzoxazolyl, benzothiazolyl, benzothiadiazolyl, benzoxadiazolyl, carbazolyl, indolyl, tetrahydroindolyl, azaindolyl, imidazopyridyl, qunizaolinyl, purinyl, pyrrolo[2,3]pyrimidyl, pyrazolo[3,4]pyrimidyl, benzo(b)thienyl, and the like. These heteroaryl groups may be optionally substituted with one or more substituents.

Suitable substituents for various groups described herein, e.g., alkyl, alkoxy, alkyl sulfanyl, alkylamino, dialkylamino, alkylene, alkenyl, alkynyl, cycloalkyl, cycloalkenyl, heterocyclyl, aryl, aralkyl, heteroaryl, and heteroarylalkyl groups, include any substituent that will form a stable compound. Examples of substituents include alkyl, alkoxy, alkyl sulfanyl, alkylamino, dialkylamino, alkenyl, alkynyl, cycloalkyl, an cycloalkenyl, an heterocyclyl, an aryl, an heteroaryl, an aralkyl, an heteroaralkyl, a haloalkyl, —C(O)NR$^a$R$^b$, —NR$^c$C(O)R$^d$, halo, —OR$^c$, cyano, nitro, haloalkoxy, —C(O)R$^c$, —NR$^a$R$^b$, —SR$^c$, —C(O)OR$^c$, —OC(O)R$^c$, —NR$^c$C(O)NR$^a$R$^b$, OC(O)NR$^a$R$^b$, NR$^c$C(O)OR$^d$, S(O)$_p$R$^c$, or —S(O)$_p$NR$^a$R$^b$, wherein R$^a$ and R$^b$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl; or R$^a$ and R$^b$ taken together with the nitrogen to which they are attached form optionally substituted heterocyclyl or optionally substituted heteroaryl; and $R^c$ and $R^d$ for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl. In addition, alkyl, cycloalkyl, alkylene, heterocyclyl, and any saturated portion of a alkenyl, cycloalkenyl, alkynyl, aralkyl, or heteroaralkyl group, may also be substituted with =O, =S, or =NR$^c$.

Choices and combinations of substituents and variables envisioned by embodiments described herein are only those that result in the formation of stable compounds. The term "stable" refers to compounds which possess stability sufficient to allow manufacture and which maintains the integrity of the compound for a sufficient period of time to be useful for the purposes detailed herein (e.g., incorporation within devices such as OLEDs). Typically, such compounds are stable at a temperature of 40° C. or less, in the absence of excessive moisture, for at least one week. Such choices and combinations will be apparent to those of ordinary skill in the art and may be determined without undue experimentation.

Unless indicated otherwise, the compounds described herein containing reactive functional groups (such as, without limitation, carboxy, hydroxy, and amino moieties) also include protected derivatives thereof. "Protected derivatives" are those compounds in which a reactive site or sites are blocked with one or more protecting groups. Suitable protecting groups for carboxy moieties include benzyl, tert-butyl, and the like. Suitable protecting groups for amino and amido groups include acetyl, tert-butoxycarbonyl, benzyloxycarbonyl, and the like. Suitable protecting groups for hydroxy include benzyl and the like. Other suitable protecting groups are well known to those of ordinary skill in the art and include those found in T. W. Greene, PROTECTING GROUPS IN ORGANIC SYNTHESIS, John Wiley & Sons, Inc. 1981, the entire teachings of which are incorporated herein by reference for all purposes.

Compounds described herein may also be in salt form. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1' methylene bis(2 hydroxy 3 naphthoate)) salts. In some cases, the salt may be formed from a compound described herein having an acidic functional group, such as a carboxylic acid functional group, and an inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy substituted mono, di, or trialkylamines; dicyclohexylamine; tributyl amine; pyridine; N methyl,N ethylamine; diethylamine; triethylamine; mono, bis, or tris (2 hydroxy lower alkyl amines), such as mono, bis, or tris (2 hydroxyethyl)-amine, 2 hydroxy tert butylamine, or tris (hydroxymethyl)methylamine, N, N, di lower alkyl N (hydroxy lower alkyl) amines, such as N,N dimethyl N (2 hydroxyethyl)-amine, or tri (2 hydroxyethyl)amine; N methyl D glucamine; and amino acids such as arginine, lysine, and the like.

In some cases, the salt may be prepared from a compound described herein having a basic functional group, such as an amino functional group, and an inorganic or organic acid. Suitable acids include, but are not limited to, hydrogen sulfate, citric acid, acetic acid, oxalic acid, hydrochloric acid, hydrogen bromide, hydrogen iodide, nitric acid, phosphoric acid, isonicotinic acid, lactic acid, salicylic acid, tartaric acid, ascorbic acid, succinic acid, maleic acid, besylic acid, fumaric acid, gluconic acid, glucaronic acid, saccharic acid, formic acid, benzoic acid, glutamic acid, methanesulfonic acid, ethanesulfonic acid, benzenesulfonic acid, and p-toluenesulfonic acid.

EXAMPLES AND EMBODIMENTS

Example 1

The following example describes the synthesis of 2,6,14-trinitrotriptycene. To a 500 mL round bottom flask equipped with a magnetic stir bar was added 200 mL of 70% nitric acid. The flask was then cooled to 0° C. in an ice bath. While stirring, 10 g of triptycene was added slowly to the flask. The mixture was stirred for 2 h after which it was equipped with a reflux condenser and placed into an 80° C. bath for 4 h with efficient stirring. After approximately 30 min the reaction mixture became a pale yellow, homogenous solution. The flask was then removed from the oil bath and the resulting brown solution was poured onto 500 mL of a mixture of ice and water yielding a white suspension. The mixture was stirred for approximately 30 minutes and then filtered to collect the white material. The solid was then washed with 500 mL of water to remove trace amounts of nitric acid. The resulting solid was then transferred to a 200 mL round bottom flask and dissolved in ethyl acetate. The resulting biphasic solution was transferred to a separatory funnel and the aqueous phase was drained off. The yellow organic phase was then washed with 50 mL of brine twice. The organic phase was transferred to a 1 L Erlenmeyer flask and dried over MgSO$_4$.

The mixture was then filtered into a 2 L round bottom flask and the solvent was removed under reduced pressure with the aid of a rotary evaporator resulting in a pale yellow foam. The foam was then dissolved in EtOAc and the yellow liquid was then loaded on 30 g of silica in a 200 mL round bottom flask. The solvent was once again removed under reduced pressure with the aid of a rotatory evaporator. The resulting pale yellow solid was then dried under high vacuum (100 mTorr) at 50° C. for 12 h (NOTE: omission of this step may complicate purification via column chromatography). The dry solid was then purified via silica gel chromatography (EtOAc:hexanes 15%→30%). Only fractions containing 2,6,14-trinitrotriptycene were collected.

While it is possible to collect 2,7,14-trinitrotriptycene as well in the later fractions, the compound may crystallize out of solution quickly. As such, the fractions may be collected immediately and the solvent may be removed as soon as possible to avoid difficulties in the collection. The solvent was removed under reduced pressure with the aid of a rotary evaporator and the resulting yellow foam was transferred to a 200 mL round bottom flask and dried under high vacuum (100 mTorr) at 50° C. for 12 h. Dichloromethane (20 mL) was then added to the foam resulting in a pale yellow solution. The flask was then placed into a sonicator at which point a pale yellow solid precipitated out. The flask was cooled to −78° C. for 5 minutes and the mixture was filtered to collect a pale yellow solid (10.2 g, 67% yield, ~90% purity, major contaminant is 2,7-dinitrotriptycene). The filtrate may then be concentrated and once again resubjected to sonication to provide an additional 1 g of product. $^1$H NMR conformed to known literature.

Example 2

The following example describes the synthesis of 2,6,14-triaminotriptycene. To a 500 mL round bottom flask equipped with a stir bar was added 2 g of 2,6,14-trinitrotriptycene and 26 g of $SnCl_2.(H_2O)_2$. 200 mL of EtOH (200 proof) was then added to the solid mixture followed by 50 mL of concentrated HCl. The flask was then equipped with a reflux condenser and placed into a preheated oil bath at 100° C. with stirring. The reaction mixture quickly became homogenous and after several hours a white precipitate began to form. After 24 h, the flask was removed from the oil bath and allowed to cool to room temperature. The white solid was then filtered and washed with 300 mL of EtOH and allowed to air dry. The solid was then collected, dissolved in 50 mL of water and poured into a separatory funnel containing 200 mL of saturated aqueous $NaHCO_3$ solution and 300 mL of EtOAc. A solid quickly formed and then dissolved into the organic layer. The aqueous phase was then tested to ensure a basic pH and is then extracted twice with 50 mL of EtOAc. The organic layers were then combined and washed twice with 50 mL brine. The yellow solution was then dried over $MgSO_4$, filtered and the solvent was removed under reduced pressure with the aid of a rotary evaporator. The resulting white solid was then redissolved in methanol and transferred to a 20 mL vial. The solvent was once again removed under reduced pressure with the aid of a rotary evaporator. The vial was then placed under high vacuum (100 mTorr) with heating (80° C.) for 12 hours (875 mg, 57%, >97% purity).

Example 3

The following example describes the synthesis of $N^2,N^6,N^{14}$-tris(2-chlorophenyl)-2,6,14-triaminotriptycene (1). 2,6,14-Triaminotriptycene (1.196 g, 4 mmol, with essentially all trace amounts of solvent from the solid), DavePhos-Bruno-Precatalyst (274 mg, 0.36 mmol, 9 mol %, 3 mol % per C—N bond), and NaOtBu (570 mg, 6 mmol, 1.5 equiv.) were added to an oven dried 16 mL test tube with Teflon screw cap equipped with two magnetic stir bars. The tube was sealed and evacuated and refilled with Ar (3×). 1-Bromo-2-chlorobenzene (580 µL, 5 mmol, 1.2 equiv.) was then injected under pressure of Ar quickly followed by dry 1,4-dioxane (8 mL). The mixture was then vigorously shaken to free the stir bars and the tube was placed into a preheated 100° C. oil bath with efficient stirring. The reaction mixture very quickly turned green and then red. After 2 h the tube was removed from the oil bath and allowed to cool to room temperature. The tube was opened, diluted with dichloromethane and filtered through a pad of $SiO_2$ into a 200 mL round bottom flask. Solvent was removed under reduced pressure with the aid of a rotary evaporator to produce a dark oil. The flask was then placed under high vacuum (100 mTorr) with heating (80° C.) for 12 hours. In some cases, it was helpful to remove all trace amounts of 1,4-dioxane to simplify purification via column chromatography. The resulting dark colored solid was then redissolved in dichloromethane and loaded onto silica gel. Solvent was once again removed under reduced pressure with the aid of a rotary evaporator and once again placed under high vacuum with heating (50° C.) until the vacuum gauge read no more than 200 mTorr. The solid was then purified via flash column chromatography on a Biotage Isolera 4 using SNAP 100 g prepacked silica cartriges and a solvent gradient of dichloromethane:hexanes (10→40%, 40 CV). For convenience, the silica gel loaded with compound may be split into two and purified separately; the fractions containing product may be then combined to afford the pure compound as a white solid (1.44 g, 57% yield, >99% purity).

Example 4

The following example describes the synthesis of 7,13,15,21-tetrahydro-5H-7,15-[3,4]epicarbazolobenzo[1,2-b:4,5-b']dicarbazole (TTC). $N^2,N^6,N^{14}$-tris(2-chlorophenyl)-2,6,14-triaminotriptycene (630 mg, 1 mmol), tricyclohexylphosphine-Bruno-Precatalyst (195 mg, 30 mol %, 10 mol % per C—C bond), $K_2CO_3$ (1.24 g, 9 mmol, 9 equiv., finely ground and oven dried) and PivOH (91.8 mg, 0.9 mmol, 0.9 equiv., 30 mol % per C—C bond) were added to an oven dried 16 mL test tube with Teflon screw cap equipped with two stir bars. The tube was sealed and evacuated and refilled with Ar (3×). Dimethylacetamide (DMA) (10 mL, 0.1M) was then added under pressure of Ar. The tube was then placed into a preheated 110° C. oil bath with efficient stirring. The reaction mixture slowly became yellow in color and eventually black. After 16 hours, the reaction tube was removed from the oil bath and allowed to cool to room temperature. The resulting black liquid was poured onto 150 mL of brine and extracted with $Et_2O$. This process typically involved approximately 1-1.5 L of $Et_2O$. The combined organic fractions were then washed twice with 200 mL of brine, dried over $MgSO_4$, and filtered. Solvent was removed under reduced pressure with the aid of a rotary evaporator to yield a reddish foam or oil. The solid was redissolved in dichloromethane, transferred to a 50 mL flask, and the solvent was once again removed under reduced pressure with the aid of a rotary evaporator. The flask was then placed under high vacuum with heating (130° C.) until the vacuum gauge read less than 200 mTorr. The flask was then allowed to cool to room temperature under ambient pressure. $Et_2O$ (10 mL) was then added to the flask and the resulting mixture was placed under sonication until the mixture became a homogenous white solid suspended in a red solution. The flask was capped and then placed into a freezer (−25° C.) for 12 hours. The flask was removed, cooled further to −78° C. and the resulting mixture was filtered and washed with cold Et$_2$O (10 mL, 3×). The tan solid was then collected and dried under high vacuum (387 mg, 74%, ~80% purity). The solid may then be carried on or further purified via recrystallization (1 mL toluene/10 mg of compound, 130° C., efficiency of ~90%) until >99.9% purity is attained. The mother liquor resulting from the crystallizations may be collected and resubjected to the purification procedure.

Example 5

The following example describes the synthesis of 5,13, 21-tri-p-tolyl-7,13,15,21-tetrahydro-5H-7,15-[3,4]epicarbazolobenzo[1,2-b:4,5-b']dicarbazole (p-Tol-TTC). TTC (521 mg, 1 mmol), K$_2$CO$_3$ (1.24 g, 9 mmol, 9 equiv., 3 equiv. per C—N bond), and tri-t-butylphosphine-Bruno-Precatalyst (171 mg, 30 mol %, 10 mol % per C—N bond) were added to an oven dried 16 mL test tube with Teflon screw cap equipped with two stir bars. The tube was sealed and evacuated and refilled with Ar (3×). p-Bromotoluene (684 mg, 4 mmol, 4 equiv.) was added via syringe under pressure of Ar. Dioxane (6 mL) was then added and the tube was placed into a preheated 110° C. oil bath with stirring. After 18 h, the tube was removed from the oil bath and allowed to cool to room temperature. A small aliquot (10 μL) was removed under pressure of Ar and tested for the presence of starting material with the aid of either TLC or HPLC. The silvery colored reaction mixture was then filtered through a pad of SiO$_2$ and washed with dichloromethane (300 mL) until no more product remained on the silica. The solvent was removed under reduced pressure with the aid of a rotary evaporator. The flask was then placed under high vacuum (100 mTorr) with heating (80° C.) for 12 h. The flask was then allowed to cool to room temperature and dichloromethane was added under ambient pressure. The dark liquid was then loaded onto silica. The solvent was once again removed with the aid of a rotary evaporator and placed under high vacuum and heating (80° C.) until the vacuum gauge read less than 200 mTorr. The compound was then purified via flash column chromatography on a Biotage Isolera 4 using SNAP 100 g prepacked silica cartridges and a solvent gradient of dichloromethane:hexanes (15→35%, 40 CV). The fractions containing product were collected into a 1 L flask and the solvent was removed under reduced pressure with the aid of a rotary evaporator. The resulting solid was then tested for purity via HPLC (12% EtOAc:Hexanes, 5 μm SiO$_2$, 15 min). If the purity was less than 99.9%, the solid may be loaded onto silica once again and purified using a SNAP ULTRA 340 g prepacked cartridge EtOAc:Hexanes (0→20%, 20 CV). Each fraction was then tested via HPLC to determine purity. The resulting compound was a white solid (487 mg, 62%, >99.9% purity).

Having thus described several aspects of some embodiments of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed:

1. A composition, comprising:
an iptycene-based compound comprising an iptycene core including one or more phenyl rings and at least one optionally substituted heterocyclyl or optionally substituted heteroaryl moiety bonded to the iptycene core, wherein the optionally substituted heterocyclyl or optionally substituted heteroaryl moiety defines at least a portion of the iptycene core,
wherein the iptycene-based compound comprises one or more carbazole moieties, and
wherein at least one of the carbazole moieties includes at least one of the phenyl rings of the iptycene core.

2. A composition as in claim 1, comprising:
a compound having one of the following structures,

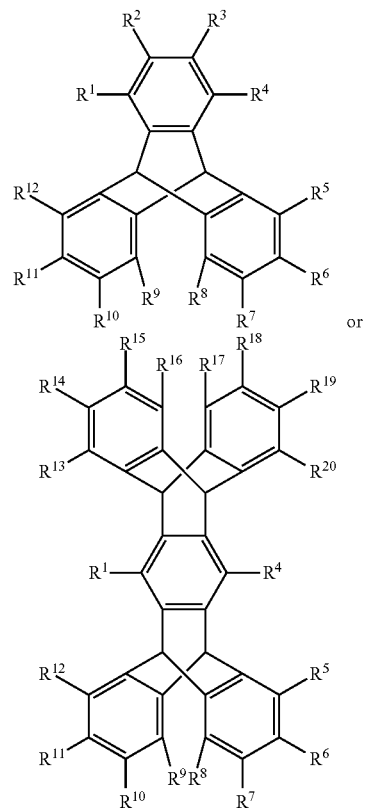

wherein:
$R^1$-$R^{20}$ can be the same or different and are hydrogen, halo, hydroxyl, amino, alkyl, heteroalkyl, alkenyl, alkynyl, aryl, heteroaryl, heterocyclyl, or a carbonyl group, any of which is optionally substituted, or, any two adjacent groups of $R^1$-$R^{20}$ can be joined together to form an optionally substituted ring,
provided that two adjacent groups of $R^1$-$R^{20}$ are joined together to form a ring, such that a carbazole moiety is formed including the phenyl ring of the core iptycene structure.

3. A composition as in claim 1, wherein the compound has the following formula,

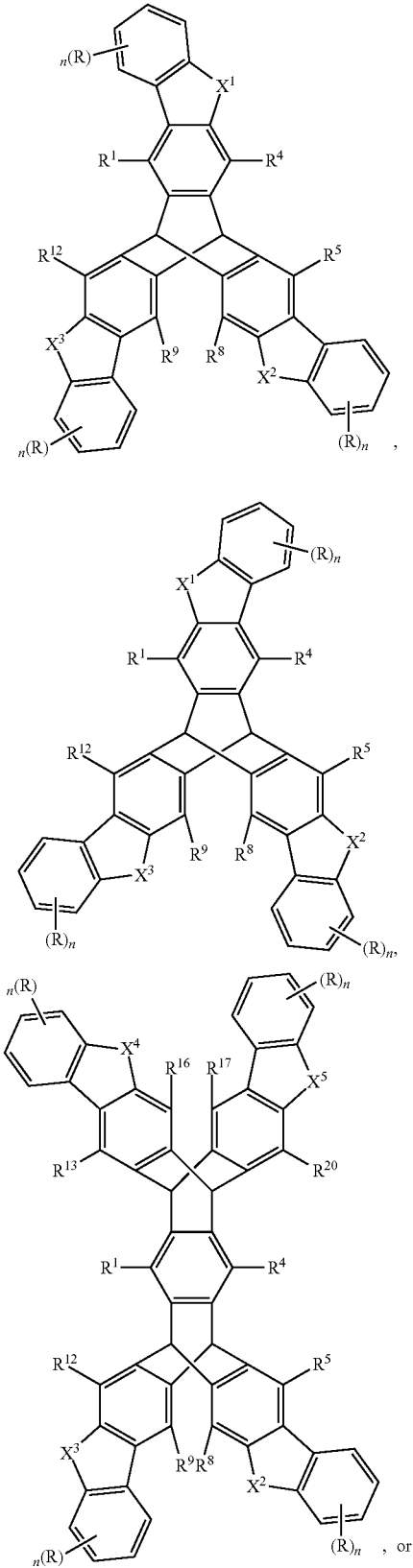

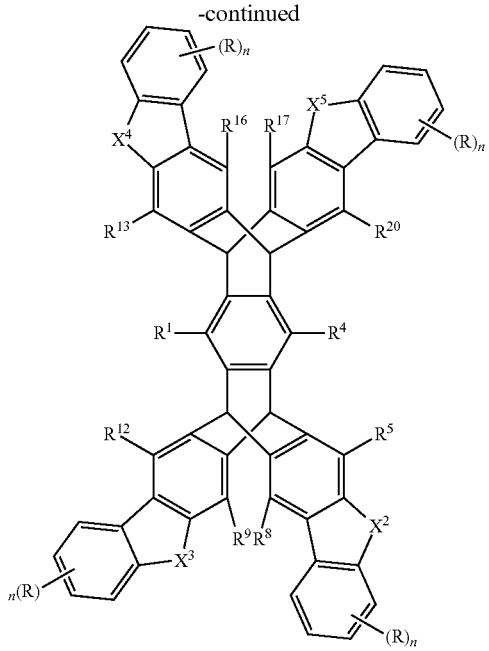

wherein:
X$^1$-X$^5$ can be the same or different and are heteroatoms or metal atoms, any of which is optionally substituted or optionally bonded to a polymer;

R$^1$, R$^4$, R$^5$, R$^8$, R$^9$, R$^{12}$, R$^{13}$, R$^{16}$, R$^{17}$, and R$^{20}$ can be the same or different and are hydrogen, halo, hydroxyl, amino, alkyl, heteroalkyl, alkenyl, alkynyl, aryl, heteroaryl, heterocyclyl, or a carbonyl group, any of which is optionally substituted or optionally bonded to a polymer;

each R can be the same or different and is a substituent, optionally substituted or optionally bonded to a polymer; and n is an integer from 0-4.

4. A composition as in claim 3, wherein R$^1$, R$^4$, R$^5$, R$^8$, R$^9$, R$^{12}$, R$^{13}$, R$^{16}$, R$^{17}$, and R$^{20}$ are hydrogen and each X$^1$-X$^5$ is NH or N(R'), wherein R' is an optionally substituted aryl or an optionally substituted heteroaryl.

5. A composition as in claim 4, wherein R' is phenyl substituted with one or more electron-withdrawing groups.

6. A composition as in claim 5, wherein R' is a group having the following formula,

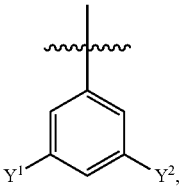

wherein Y$^1$ and Y$^2$ can be the same or different and are hydrogen, halo, cyano, fluoroalkyl, fluoroalkoxy, or a carbonyl group.

7. A composition as in claim 6, wherein R' is a group having the following formula,

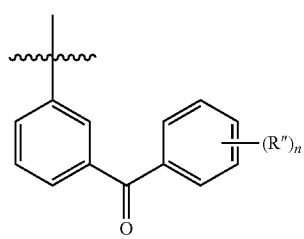

or

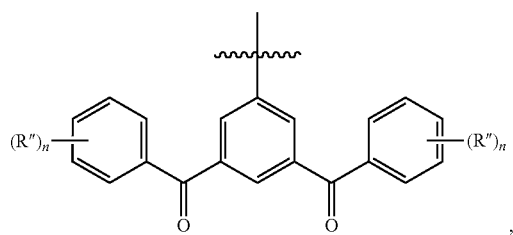, wherein R" is alkyl, fluoroalkyl, alkoxy, fluoroalkoxy, and n is 0-5.

8. A composition as in claim 6, wherein R' is a group having the following formula,

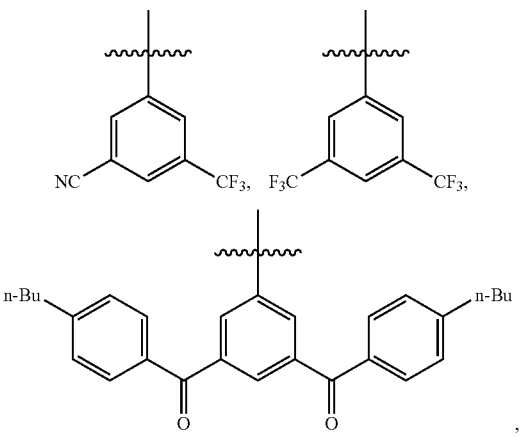

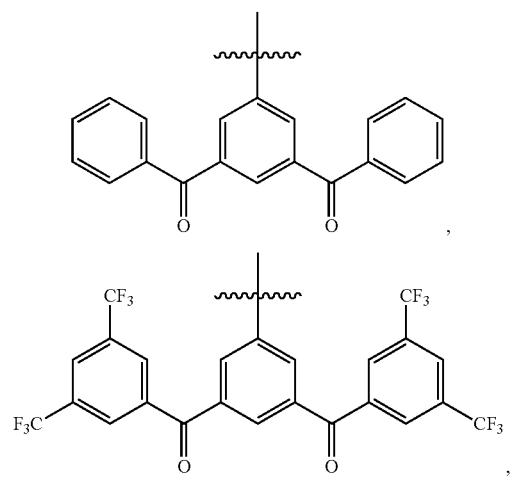,

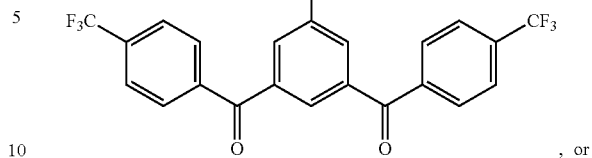, or

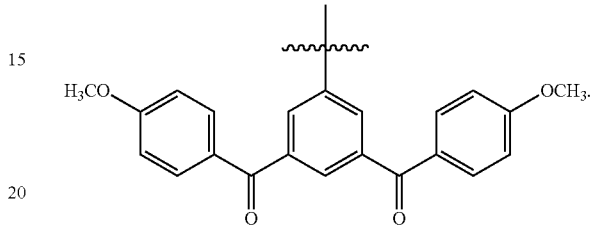

9. A composition as in claim 4, wherein R' is phenyl substituted with one or more electron-donating groups.

10. A composition as in claim 9, wherein the electron-donating group is alkyl, alkoxy, aryl, heteroaryl, P(aryl)$_3$, or Si(aryl)$_3$.

11. A composition as in claim 10, wherein R' is phenyl substituted with methyl, Phenyl,

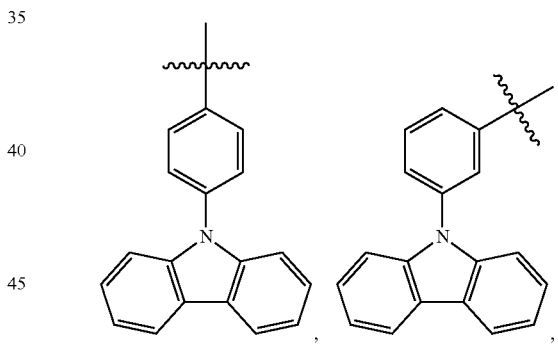

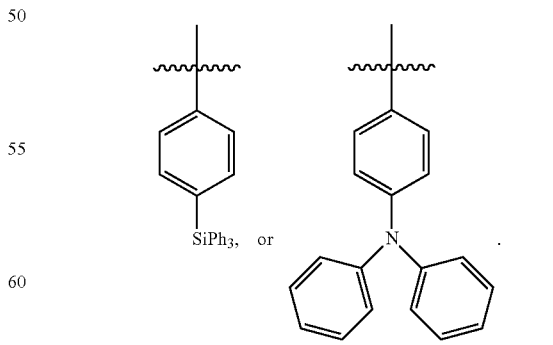

12. A composition as in claim 1, wherein the compound has the following structure,

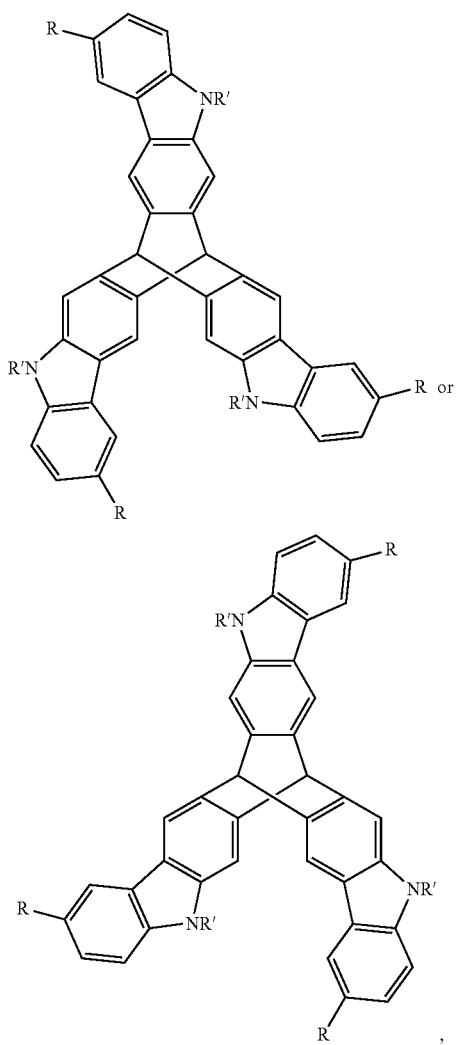

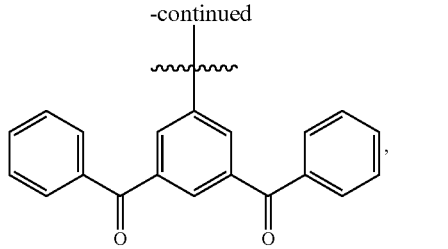

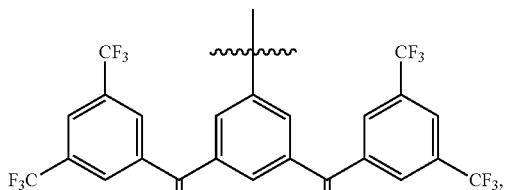

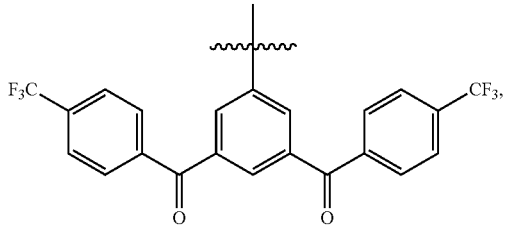

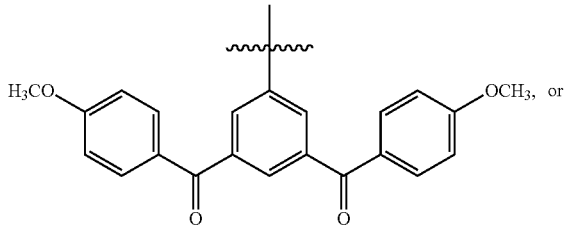

wherein:

R is hydrogen, alkyl, alkoxy, fluoroalkyl, or fluoroalkoxy; and

R' is a group having the following formula,

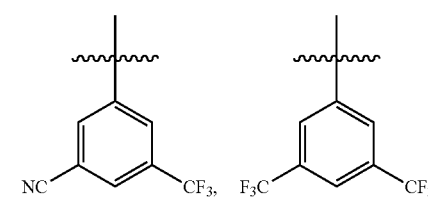

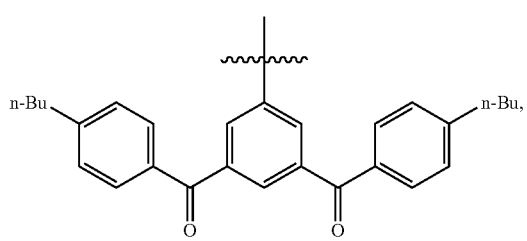

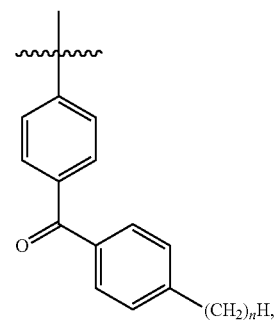

wherein n is 1 or greater.

13. A composition as in claim 12, wherein R is hydrogen, O-butyl, or $CF_3$.

14. A composition as in claim 13, wherein n is 1-10.

15. A composition as in claim 1, wherein the compound is bonded to a polymer or is dispersed within a polymer.

16. A device, comprising:
an iptycene-based compound comprising an iptycene core including one or more phenyl rings and at least one heterocyclyl or heteroaryl moiety bonded to the iptycene core, wherein the heterocyclyl or heteroaryl moiety is substituted with at least one electron-withdrawing group and the iptycene-based compound exhibits a solid state singlet-triplet energy gap of about 1 kcal/mol or less; and two electrodes constructed and arranged to be in electrochemical communication with the iptycene-based compound, wherein the iptycene-based compound comprises one or more carbazole moieties, and wherein at least one of the carbazole moieties includes at least one of the phenyl rings of the iptycene core.

17. A device as in claim 16, wherein the iptycene-based compound exhibits a solid state singlet-triplet energy gap of about 0.5 kcal/mol or less.

18. A device as in claim 16, wherein the device is an organic light-emitting diode or an organic photovoltaic device.

19. A device as in claim 16, wherein the iptcyene-based compound has the following structure,

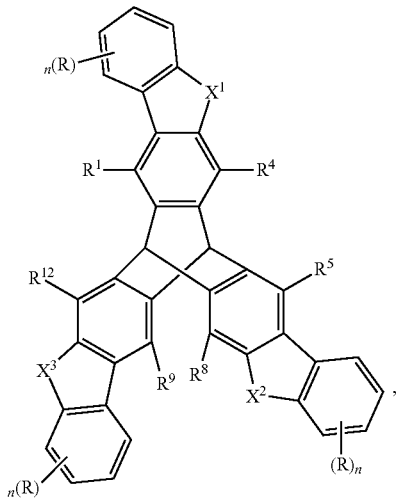

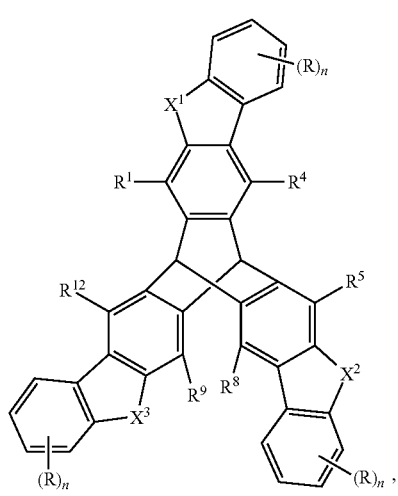

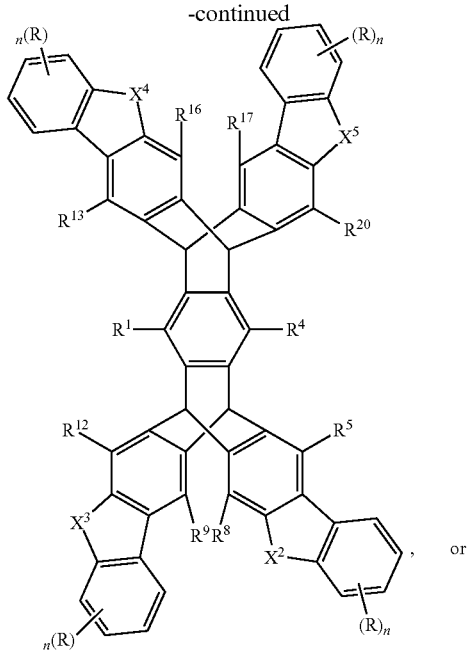

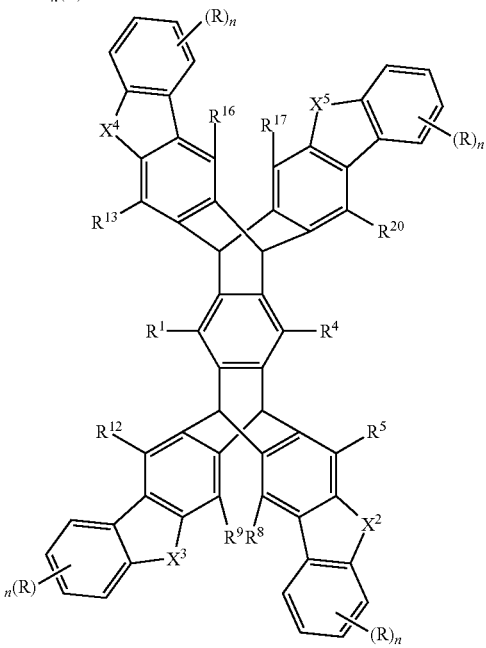

wherein:
X$^1$-X$^5$ can be the same or different and are heteroatoms or metal atoms, any of which is optionally substituted or optionally bonded to a polymer;

R$^1$, R$^4$, R$^5$, R$^8$, R$^9$, R$^{12}$, R$^{13}$, R$^{16}$, R$^{17}$, and R$^{20}$ can be the same or different and are hydrogen, halo, hydroxyl, amino, alkyl, heteroalkyl, alkenyl, alkynyl, aryl, heteroaryl, heterocyclyl, or a carbonyl group, any of which is optionally substituted or optionally bonded to a polymer;

each R can be the same or different and is a substituent, optionally substituted or optionally bonded to a polymer; and n is an integer from 0-4.

20. A device as in claim 16, wherein the iptcyene-based compound has the following formula,

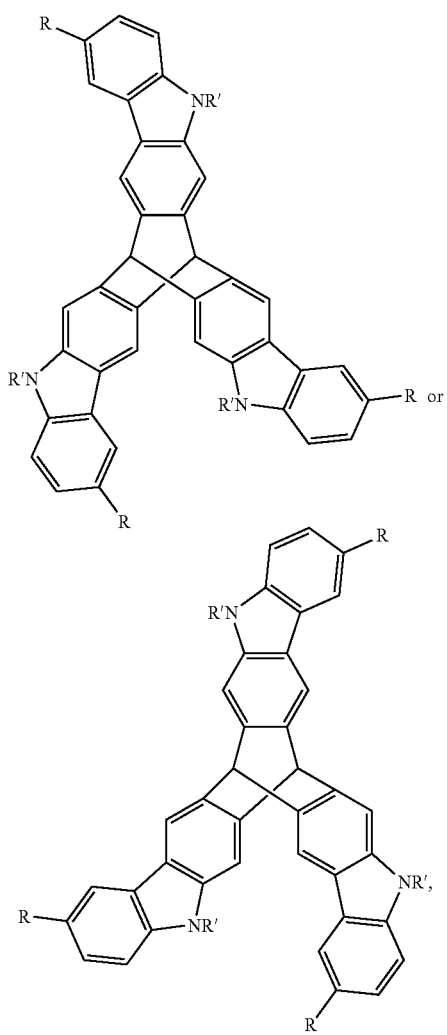
wherein:
R is hydrogen, alkyl, alkoxy, fluoroalkyl, or fluoroalkoxy; and
R' is a group having the following formula,
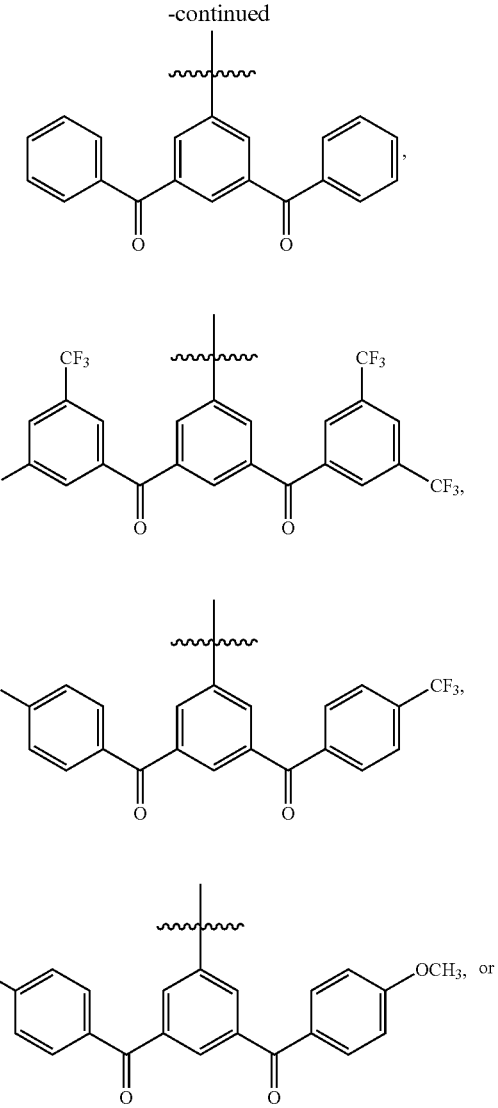
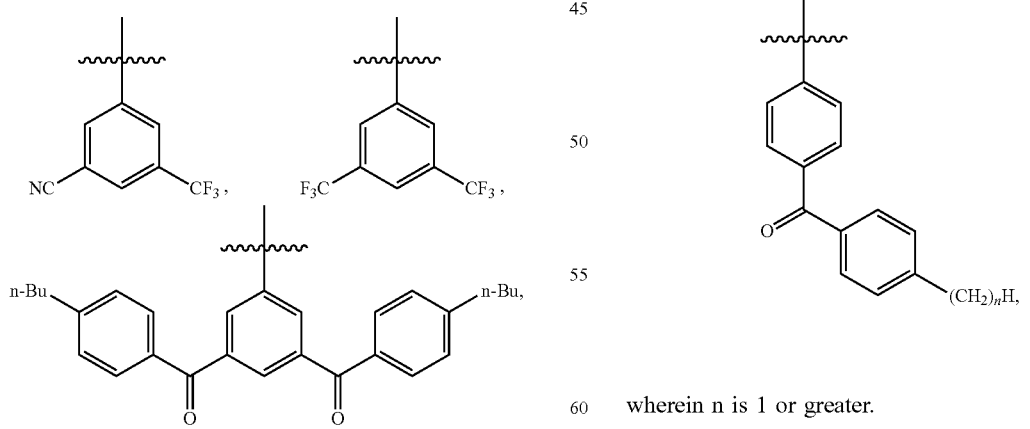
wherein n is 1 or greater.
* * * * *

UNITED STATES PATENT AND TRADEMARK OFFICE
CERTIFICATE OF CORRECTION

PATENT NO.         : 9,595,682 B2
APPLICATION NO.    : 14/067342
DATED              : March 14, 2017
INVENTOR(S)        : Stephen L. Buchwald et al.

It is certified that error appears in the above-identified patent and that said Letters Patent is hereby corrected as shown below:

In the Claims

In Claim 11, at Column 26, Line 32, "Phenyl" should be replaced with -- phenyl --

Signed and Sealed this
Thirtieth Day of January, 2018

Joseph Matal
*Performing the Functions and Duties of the*
*Under Secretary of Commerce for Intellectual Property and*
*Director of the United States Patent and Trademark Office*